United States Patent
Yip et al.

(10) Patent No.: US 9,656,089 B2
(45) Date of Patent: May 23, 2017

(54) METHOD FOR AUTOMATION OF THERAPY-BASED PROGRAMMING IN A TISSUE STIMULATOR USER INTERFACE

(71) Applicant: BOSTON SCIENTIFIC NEUROMODULATION CORPORATION, Valencia, CA (US)

(72) Inventors: Anita Yip, Los Angeles, CA (US); Prakash Rao, Philadelphia, PA (US); Dennis Zottola, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 329 days.

(21) Appl. No.: 14/099,734

(22) Filed: Dec. 6, 2013

(65) Prior Publication Data
US 2014/0172045 A1 Jun. 19, 2014

Related U.S. Application Data

(60) Provisional application No. 61/737,694, filed on Dec. 14, 2012.

(51) Int. Cl.
*A61N 1/372* (2006.01)
*A61N 1/36* (2006.01)

(52) U.S. Cl.
CPC ..... *A61N 1/37247* (2013.01); *A61N 1/36185* (2013.01)

(58) Field of Classification Search
CPC .......................... A61N 1/37247; A61N 1/36185
See application file for complete search history.

(56) References Cited

U.S. PATENT DOCUMENTS 6,516,227 B1 2/2003 Meadows et al.
6,895,280 B2 5/2005 Meadows et al.
(Continued)

FOREIGN PATENT DOCUMENTS

WO WO-2014093178 A2 6/2014

OTHER PUBLICATIONS

U.S. Appl. No. 61/611,840, Entitled: System and Method for Estimating Location and Depth of Stimulation Leads, Inventor: Changfang Zhu et al., filed Mar. 16, 2012.
(Continued)

*Primary Examiner* — Mark W Bockelman
(74) *Attorney, Agent, or Firm* — Schwegman Lundberg & Woessner, P.A.

(57) ABSTRACT

A method for programming a neurostimulator includes automatically performing a series of steps. One or more control elements may be actuated to select the series of steps from a plurality of series of steps stored in a memory of an external control device. One or more control elements may be actuated during the performance of the series of steps in order to cause one of the steps to pause, stop, restart, skip, or repeat. The series of steps may be a series of pre-programming steps, and the method may further include programming the neurostimulator after the series of pre-programming steps is performed. An external device for programming the neurostimulator includes control circuitry configured for automatically performing the series of steps, and a user interface including the one or more control elements configured for being actuated. The control device also includes the memory for storing the plurality of series of steps.

20 Claims, 10 Drawing Sheets

(56) References Cited

U.S. PATENT DOCUMENTS

| | | |
|---|---|---|
| 6,993,384 B2 | 1/2006 | Bradley et al. |
| 2002/0082665 A1* | 6/2002 | Haller ................ A61N 1/37264 607/60 |
| 2003/0105620 A1* | 6/2003 | Bowen ................ G06F 17/5022 703/22 |
| 2006/0235472 A1* | 10/2006 | Goetz ................ A61N 1/36135 607/2 |
| 2008/0154340 A1 | 6/2008 | Goetz et al. |
| 2010/0010566 A1 | 1/2010 | Thacker et al. |
| 2010/0121409 A1 | 5/2010 | Kothandaraman et al. |
| 2011/0125214 A1 | 5/2011 | Goetz et al. |
| 2011/0307032 A1 | 12/2011 | Goetz et al. |
| 2012/0239116 A1 | 9/2012 | Lee et al. |

OTHER PUBLICATIONS

Annex to Form PCT/ISA/206, Communication Relating to the Results of the Partial International Search dated Feb. 27, 2014 for International Appl. No. PCT/US2013/073722, Applicant: Boston Scientific Neuromodulation Corporation, (2pages).

"International Application Serial No. PCT/US2013/073722, International Preliminary Report on Patentability mailed Jun. 25, 2015", 9 pgs.

\* cited by examiner

METHOD FOR AUTOMATION OF THERAPY-BASED PROGRAMMING IN A TISSUE STIMULATOR USER INTERFACE

RELATED APPLICATION DATA

The present application claims the benefit under 35 U.S.C. §119 to U.S. provisional patent application Ser. No. 61/737,694, filed Dec. 14, 2012. The foregoing application is hereby incorporated by reference into the present application in its entirety.

FIELD OF THE INVENTION

The present invention relates to tissue stimulation systems, and more particularly, to a system and method for programming an implantable tissue stimulator.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Also, Functional Electrical Stimulation (FES) systems such as the Freehand system by NeuroControl (Cleveland, Ohio) have been applied to restore some functionality to paralyzed extremities in spinal cord injury patients. Occipital Nerve Stimulation (ONS), in which leads are implanted in the tissue over the occipital nerves, has shown promise as a treatment for various headaches, including migraine headaches, cluster headaches, and cervicogenic headaches. In recent investigations, Peripheral Stimulation (PS), which includes Peripheral Nerve Field Stimulation (PNFS) techniques that stimulate nerve tissue directly at the symptomatic site of the disease or disorder (e.g., at the source of pain), and Peripheral Nerve Stimulation (PNS) techniques that directly stimulate bundles of peripheral nerves that may not necessarily be at the symptomatic site of the disease or disorder, has demonstrated efficacy in the treatment of chronic pain syndromes and incontinence, and a number of additional applications are currently under investigation. Vagal Nerve Stimulation (VNS), which directly stimulate the Vagal Nerve, has been shown to treat heart failure, obesity, asthma, diabetes, and constipation.

These implantable neurostimulation systems typically include one or more electrode carrying neurostimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension. Thus, electrical pulses can be delivered from the neurostimulator to the neurostimulation leads to stimulate the tissue and provide the desired efficacious therapy to the patient.

The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

The neurostimulation system may further include a handheld patient programmer in the form of a remote control (RC) to remotely instruct the neurostimulator to generate electrical stimulation pulses in accordance with selected stimulation parameters. The RC may, itself, be programmed by a clinician, for example, by using a clinician's programmer (CP), which typically includes a general purpose computer, such as a laptop, with a programming software package installed thereon.

A programming session may require an initial setup for programming parameters and electrode settings, and may sequence through a series of pre-determined configurations in an attempt to optimize therapy for a patient. The settings may be consistent across all programming sessions or may vary depending on therapy (i.e., DBS, PNS, sacral nerve stimulation, SCS, etc.), lead placement, or target area. Physicians and clinicians may also have their own preferred settings based on experience or values defined in the literature.

For initial settings consistent across all programming sessions, preset values can be designed into specialized screens in the software so the clinician would simply open the specialized screen to access a particular programming configuration. Alternatively, if specialized screens are not available, clinicians can be trained to perform the steps necessary to reach the settings using generic screens in the software.

One problem with these specialized screens is that there is little to no flexibility to change the settings. The needs met from a specialized screen for "common" programming settings or sequences may even change over time, and it may be difficult to establish settings that work across all applications. There, thus, remains a need for a tool that allows users to automate the setup of parameter settings, electrode configurations, and programming sequences for programming sessions so repetitive steps can be performed quickly and easily. In addition, the tool may allow users to automate the execution of user-defined steps that would sequence through a series of parameters and/or electrode configurations (e.g., current steering) during a programming session.

SUMMARY OF THE INVENTION

In accordance with one aspect of the present inventions, an external control device for programming a neurostimulator in communication with the external control device is provided. The external control device includes control circuitry configured for automatically performing a series of steps, and a user interface including one or more control elements configured for being actuated during the performance of the series of steps to prompt the control circuitry to pause, stop, restart, skip, or repeat one of the steps. The user interface may include a monitor configured for displaying which step in the series is currently being performed. The external control device may include memory configured for storing a plurality of different series of steps, and the user interface may include another one or more control elements configured for being actuated to prompt the control circuitry to select the series of steps from the stored plurality of series of steps. The user interface may include a mouse, a trackball, a touchpad, and/or a joystick configured for allowing the user to actuate the one or more control elements. The user interface may include a digitizer screen configured for allowing the user to actuate the one or more control elements. The series of steps may be a series of pre-programming steps, and the user interface may include another one or more control elements configured for being actuated to prompt the control circuitry to program the neurostimulator after the series of pre-programming steps is performed.

In accordance with another aspect of the present inventions, a method for programming a neurostimulator in communication with an external control device including one or more control elements is provided. The method includes automatically performing a series of steps, and actuating the one or more control elements during the performance of the series of steps to cause one of the steps to pause, stop, restart, skip, or repeat. The method may further include displaying which step in the series is currently being performed. The method may further include selecting the series of steps from a plurality of series of steps stored in a memory of the external control device. The series of steps may be a series of pre-programming steps, and the method may further include programming the neurostimulator after the series of pre-programming steps is performed.

In accordance with yet another aspect of the present inventions, an external control device for programming a neurostimulator in communication with the external control device is provided. The external control device includes a user interface including one or more control elements configured for being actuated, and memory configured for storing a plurality of different series of steps. The user interface may include a mouse, a trackball, a touchpad, and/or a joystick configured for allowing the user to actuate the one or more control elements. The user interface may include a digitizer screen configured for allowing the user to actuate the one or more control elements.

The external control device further includes control circuitry configured for selecting, in response to actuation of the one or more control elements, a series of steps from the stored plurality of series of steps. The selection may be based upon at least one of: target tissue, and a condition being treated. The control circuitry is further configured for automatically performing the selected series of steps. The user interface may include another one or more control elements configured for being actuated during the performance of the series of steps to prompt the control circuitry to pause, stop, restart, skip, or repeat one of the steps. The series of steps may be a series of pre-programming steps, and the user interface may include another one or more control elements configured for being actuated to prompt the control circuitry to program the neurostimulator after the series of pre-programming steps is performed. The user interface may include a monitor configured for displaying which step in the series is currently being performed.

In accordance with still another aspect of the present inventions, a method for programming a neurostimulator in communication with an external control device including one or more control elements is provided. The method includes actuating the one or more control elements to select a series of steps from a plurality of series of steps. The selection may be based upon target tissue and/or a condition being treated. The target tissue may include brain tissue, spinal cord tissue, or peripheral nerve tissue.

The method further includes automatically performing the selected series of steps. The method may further include actuating another one or more control elements of the external control device during the performance*-e of the series of steps to cause one of the steps to pause, stop, restart, skip, or repeat. The method may further include displaying which step in the series is currently being performed. The series of steps may be a series of pre-programming steps, and the method may further include programming the neurostimulator after the series of pre-programming steps is performed.

In accordance with still another aspect of the present inventions, an external control device for programming a neurostimulator in communication with the external control device is provided. The external control device includes a user interface including one or more control elements and another one or more control elements configured for being actuated. The user interface may include a mouse, a trackball, a touchpad, and/or a joystick configured for allowing the user to actuate the one or more control elements and other one or more control elements. The user interface may include a digitizer screen configured for allowing the user to actuate the one or more control elements and the other one or more control elements.

The external control device further includes control circuitry configured for, in response to actuation of the one or more control elements, automatically performing a series of pre-programming steps, and, in response to actuation of the other one or more control elements, performing at least one programming step after the series of pre-programming steps is complete. The user interface may include an additional one or more control elements configured for being actuated during the performance of the series of pre-programming steps to prompt the control circuitry to pause, stop, restart, skip, or repeat one of the pre-programming steps. The control circuitry may be further configured for preventing the neurostimulator from applying stimulation during the pre-programming steps, and for instructing the neurostimulator to apply stimulation during the programming steps.

In accordance with yet another aspect of the present inventions, a method for programming a neurostimulator in communication with an external control device is provided. The method includes actuating a control element in order to prompt the external control device to automatically perform a series of pre-programming steps. The method further includes actuating another one or more control elements to prompt the external control device to perform one or more programming steps after the series of pre-programming steps is complete. The method may further include actuating another control element in order to pause, stop, restart, skip, or repeat one of the pre-programming steps in the series.

The pre-programming steps in accordance with the aspects of the present inventions described above may include one or more of: defining one or more initial programming parameters selected from the group consisting of: pulse amplitude, pulse width, pulse frequency, pulse shape, pulse waveform, and pre-pulsing; defining at least one current steering parameter selected from the group consisting of: resolution, focus, start point, end point, directionality, and path; defining an electrode configuration; defining at least one stimulation limitation selected from the group consisting of: maximum pulse amplitude, minimum pulse amplitude, maximum pulse width, minimum pulse width, maximum pulse rate, and minimum pulse rate; and defining a configuration of a lead coupled to the neurostimulator.

In accordance with still another aspect of the present inventions, an external control device for operating a neurostimulator in communication with the external control device is provided. The external control device includes a user interface including a plurality of control elements and another one or more control elements configured for being actuated. The user interface may include a mouse, a trackball, a touchpad, and/or a joystick configured for allowing the user to actuate the plurality of control elements and the other one or more control elements. The user interface may include a digitizer screen configured for allowing the user to actuate the plurality of control elements and the other one or more control elements.

The external control device further comprises control circuitry configured for, in response to actuation of the plurality of control elements, performing a plurality of steps and recording the plurality of steps, and, in response to actuation of the other one or more control elements, automatically performing the recorded plurality of steps. At least one of the steps may be a programming step, and the control circuitry may be configured for sending a signal to the neurostimulator while the programming step is being performed. At least one of the steps may be a pre-programming step, and the control circuitry may be configured to refrain from sending a signal to the neurostimulator while the pre-programming step is being performed. The external control device may also include memory for storing the recorded plurality of steps.

In accordance with yet another aspect of the present inventions, a method for operating a neurostimulator in communication with an external control device is provided. The method includes actuating a plurality of control elements in order to prompt the external control device to perform a plurality of steps; recording the plurality of steps; and actuating another control element in order to prompt the external control device to automatically perform the recorded plurality of steps. At least one of the steps may be a programming step, and the external control device may send signals to the neurostimulator while the programming step is being performed. At least one of the steps may be a pre-programming step, and the external control device may not send signals to the neurostimulator while the pre-programming step is being performed. The method may further include storing the recorded plurality of steps in a memory component of the external control device.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
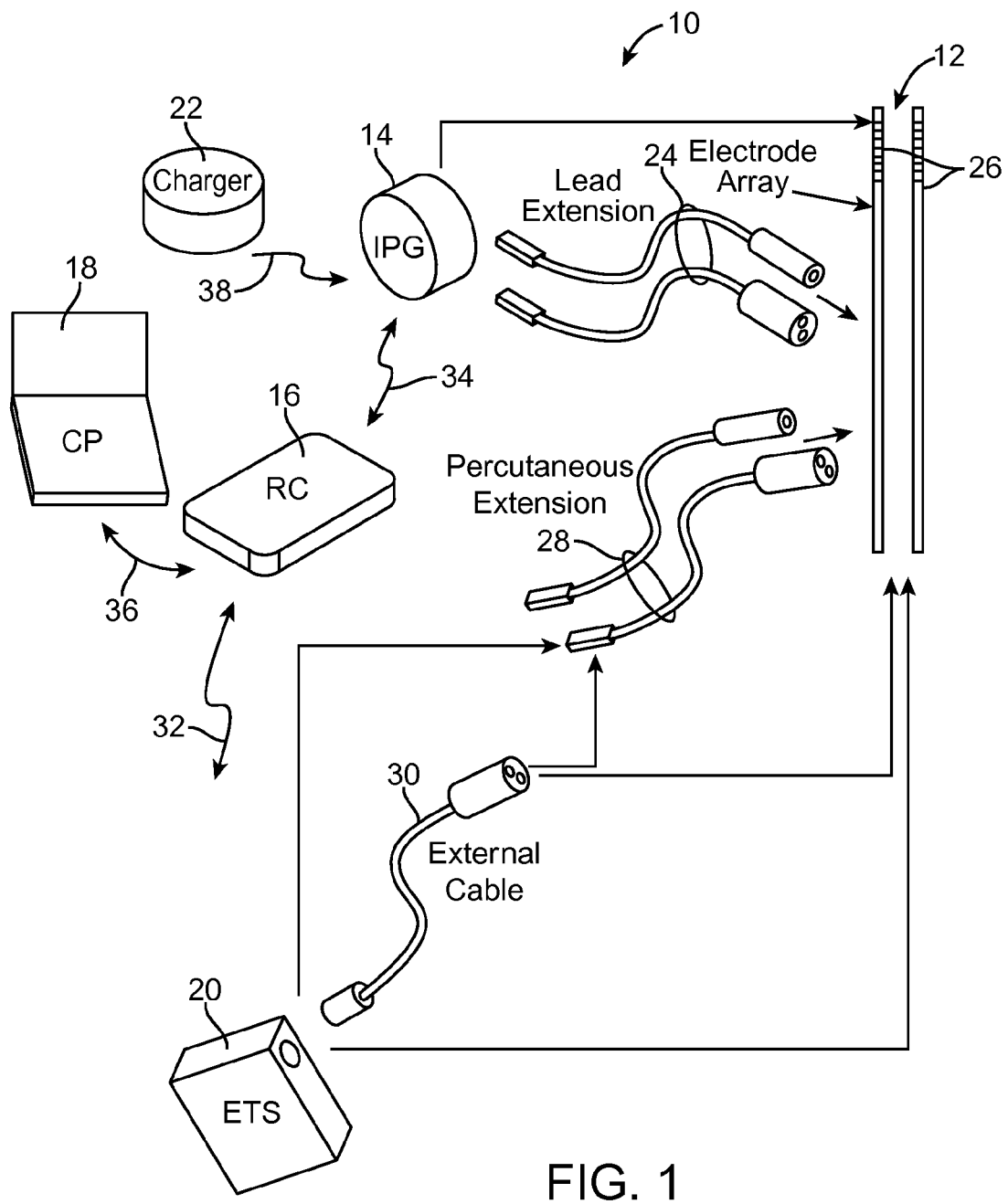
FIG. 1 is perspective view of one embodiment of a neurostimulation system arranged in accordance with the present inventions.

Turning first to FIG. 1, an exemplary neurostimulation system 10 generally includes a plurality (in this case, two) of implantable neurostimulation leads 12, an implantable pulse generator (IPG) 14, an external remote controller (RC) 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead in can be used in place of one or more of the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via percutaneous lead extensions 28 and/or an external cable 30 to the neurostimulation leads 12. The ETS 20, which has pulse generation circuitry similar to that of the IPG 14, also delivers electrical stimulation energy in the form of a pulsed electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

Figure 2:
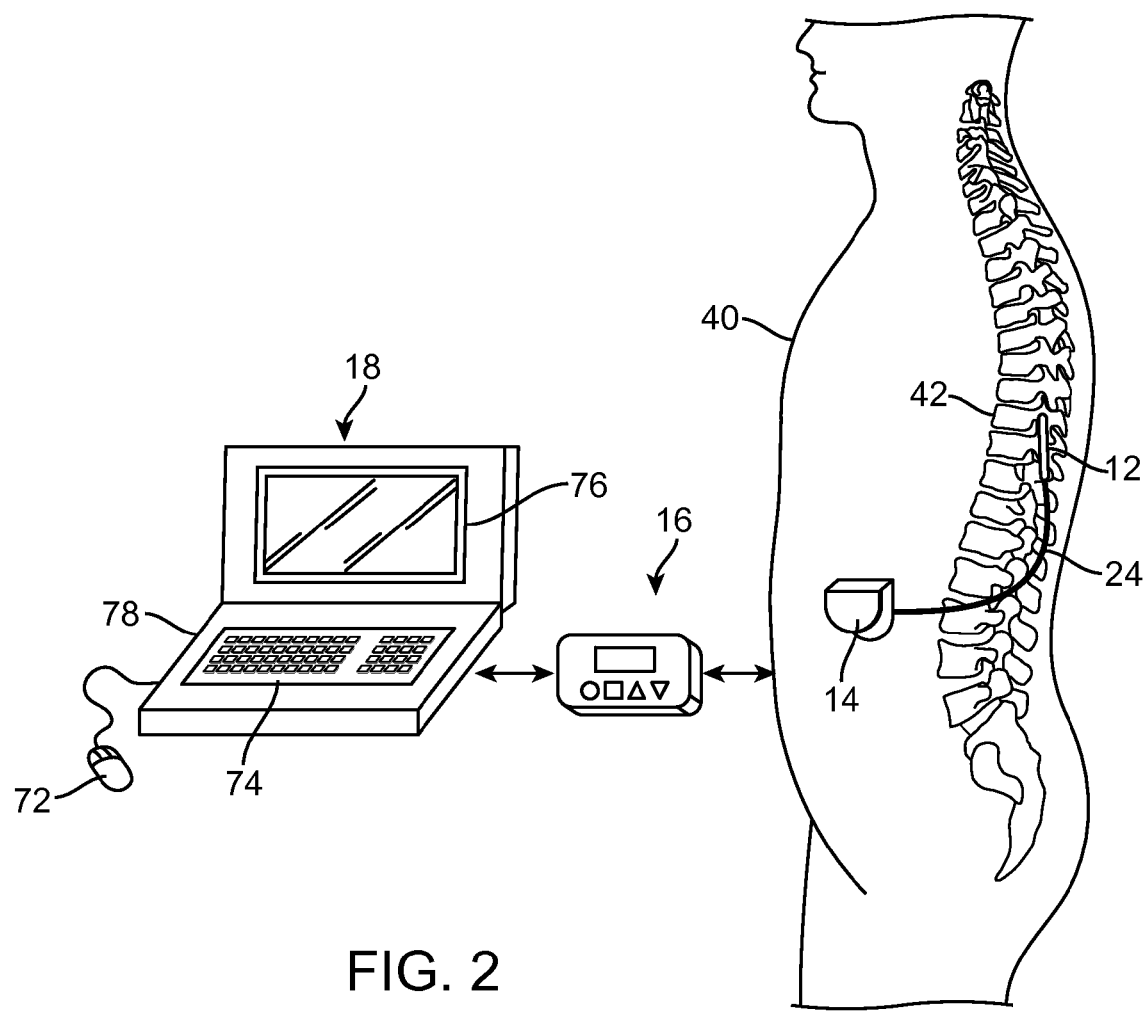
FIG. 2 is a plan view of the neurostimulation system of FIG. 1 in use with a patient.

As shown in FIG. 2, the neurostimulation system 10 is utilized in the context of a Spinal Cord Stimulation (SCS) application. To this end, the neurostimulation leads 12 are implanted within the spinal column 42 of a patient 40. The preferred placement of the neurostimulation leads 12 is adjacent, i.e., resting upon, the spinal cord area to be stimulated. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16. It should be understood that, although the neurostimulation system 10 is shown in FIG. 2 in the context of an SCS application, the neurostimulation system 10 may be utilized in the context of other therapeutic application, including Deep Brain Stimulation (DBS), Functional Electrical Stimulation (FES), Occipital Nerve Stimulation (ONS), Peripheral Nerve Stimulation (PNS), Peripheral Nerve Field Stimulation (PNFS), and Vagal Nerve Stimulation (VNS).

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the case of the IPG 14. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Tripolar stimulation occurs when three of the lead electrodes 26 are activated, two as anodes and the remaining one as a cathode, or two as cathodes and the remaining one as an anode.

In the illustrated embodiment, the IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention.

Further details discussing the detailed structure and function of IPGs are described more fully in U.S. Pat. Nos. 6,516,227 and 6,993,384, which are expressly incorporated herein by reference. For purposes of brevity, the details of the RC 16, ETS 20, and external charger 22 will not be described herein. Details of exemplary embodiments of these components are disclosed in U.S. Pat. No. 6,895,280, which is expressly incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, during a programming session, modification of the stimulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a minicomputer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

To allow the user to perform these functions, the CP 18 includes a user interface. In the illustrated embodiment, the user interface of the CP 18 includes a mouse 72, a keyboard 74, and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc, can be used to manipulate graphical objects on the display screen 76. In alternative embodiments, the display screen 76 takes the form of a digitizer touch screen.

Figure 3:
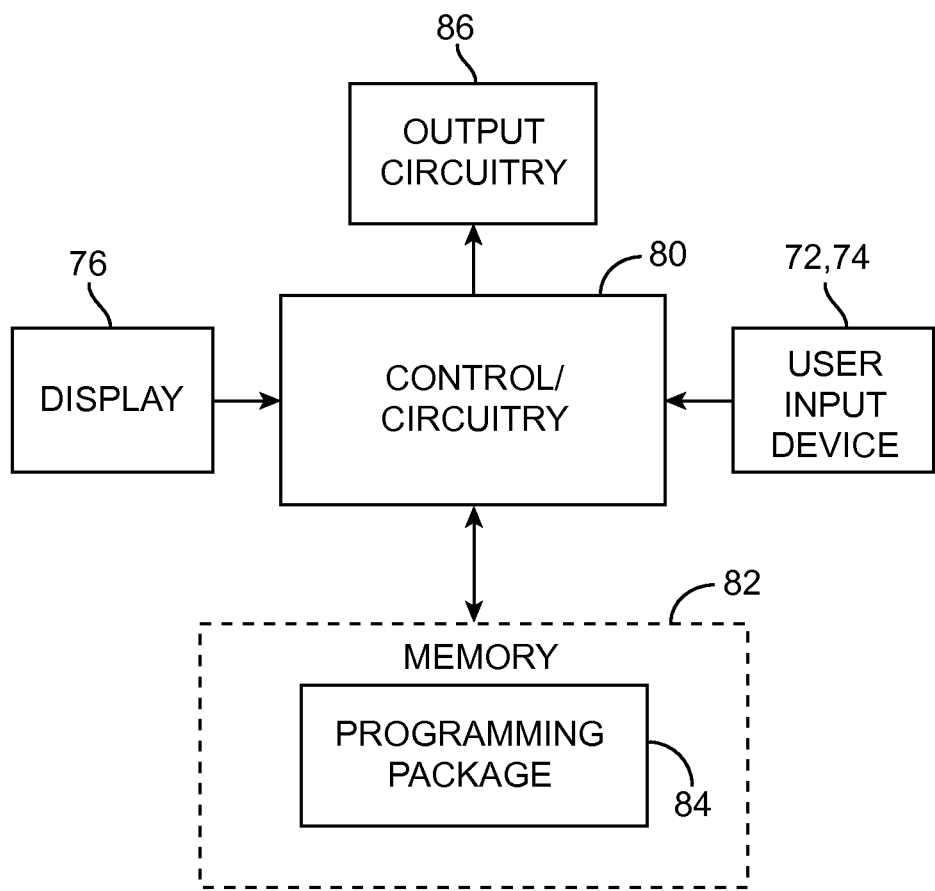
FIG. 3 is a block diagram of the components of a clinician programmer that can be used in the neurostimulation system of FIG. 1.

As shown in FIG. 3, the CP 18 generally includes control circuitry 80 (e.g., a central processor unit (CPU)) and memory 82 that stores a stimulation programming package 84, which can be executed by the control circuitry 80 to allow the user to program the IPG 14, and RC 16. The CP 18 further includes output circuitry 86 for downloading (e.g., via the telemetry circuitry of the RC 16) stimulation parameters to the IPG 14 and RC 16 and for uploading stimulation parameters already stored in memory of the RC 16, via telemetry circuitry of the RC 16.

Execution of the programming package 84 by the control circuitry 80 provides a multitude of display screens that can be navigated through via use of the mouse 72. These display screens allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. Patent Application Publication No. 2010/0010566, entitled "System and Method for Converting Tissue Stimulation Programs in a Format Usable by an Electrical Current Steering Navigator," and U.S. Patent Application Publication No. 2010/0121409, entitled "System and Method for Determining Appropriate Steering Tables for Distributing Stimulation Energy Among Multiple Neurostimulation Electrodes," which are expressly incorporated herein by reference.

Figure 4:
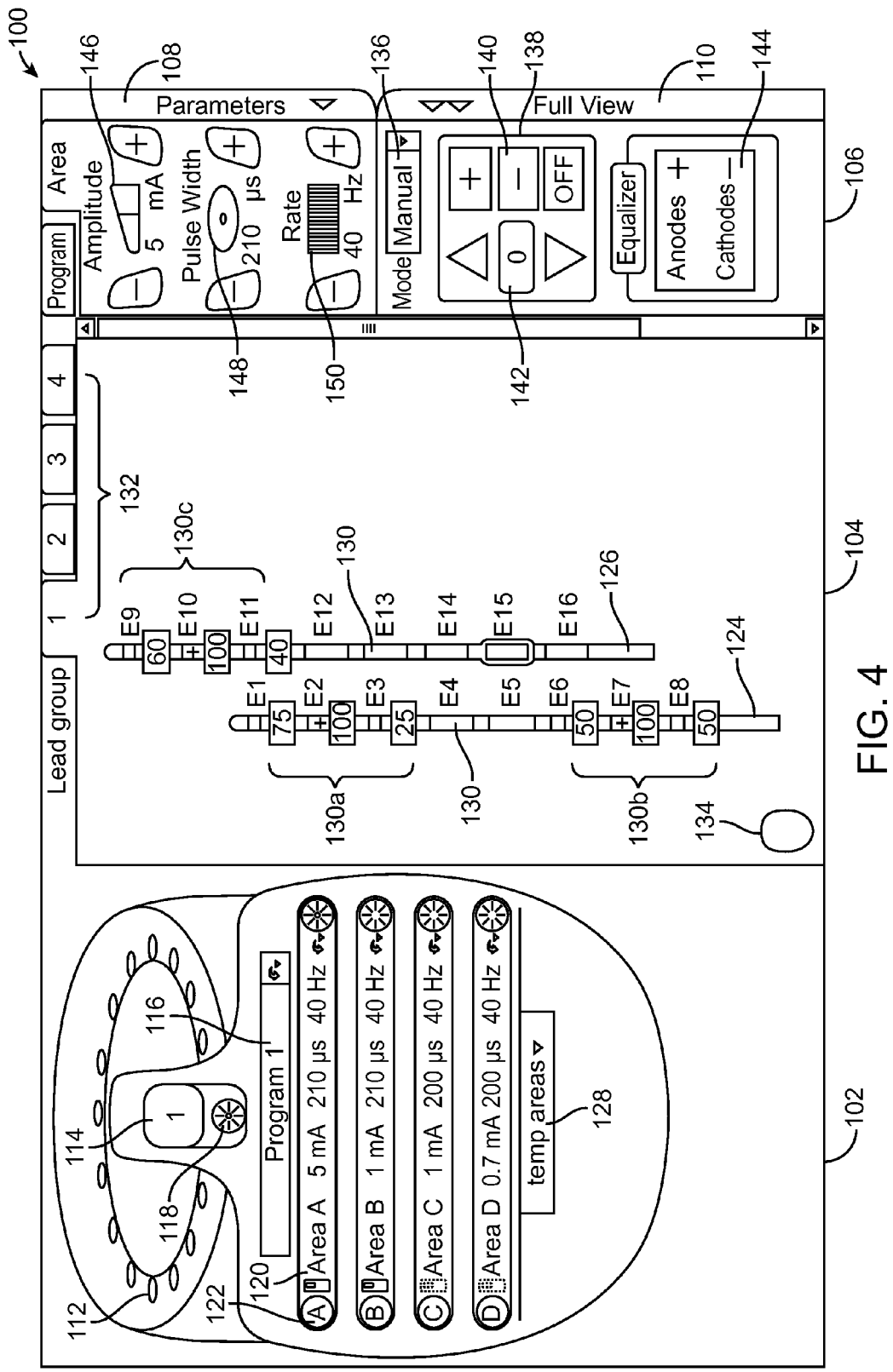
FIG. 4 is a plan view of a user interface of the CP of FIG. 3 for programming the IPG of FIG. 1 in a manual mode.

Referring now to FIG. 4, a graphical user interface (GUI) 100 that can be generated by the CP 18 to allow a user to program the IPG 14 will be described. In the illustrated embodiment, the GUI 100 comprises three panels: a program selection panel 102, a lead display panel 104, and an electrical parameter adjustment panel 106. Some embodiments of the GUI 100 may allow for closing and expanding one or both of the lead display panel 104 and the parameter adjustment panel 106 by clicking on the tab 108 (to show or hide the parameter adjustment panel 106) or the tab 110 (to show or hide the full view of both the lead display panel 104 and the parameter adjustment panel 106).

The program selection panel 102 provides information about programs and areas that have been, or may be, defined for the IPG 14. A plurality of programs may be displayed in carousel 112. In the illustrated embodiment, sixteen programs may be defined, but program 1 is the only one currently defined, as shown by the "1" in field 114. Other embodiments may use a carousel or other techniques for displaying available programs with different numbers or arrangements of available program slots.

Each program may be named, as indicated by the name field 116. A stimulation on/off button 118 allows turning the currently active program on or off. When the active program is on, stimulation parameter sets will be generated in the CP 18 and transmitted to the RC 16. Up to four program areas 120 may be defined, allowing a program to control stimulation of multiple areas. Each program area 120 may separately control stimulation of electrodes in the patient, and may be separately turned on or off. Each of the program areas 120 may be labeled with a label 122 that may be used as a marker on the graphical leads 124 and 126, as described below. A number of temporary areas 128 may be used for temporary storage of area information by copying a program area 120 into a temporary area 128 or copying a temporary area 128 into a program area 120. This allows copying a program area 120 from one of the four slots to another slot via one of the temporary areas 128. Other embodiments may also allow copying one of the program areas 120 into another one of the program areas 120 directly. Individual programs may be copied to other slots in the carousel 112 or deleted as desired.

Turning now to the lead display panel 104, graphical leads 124 and 126 are illustrated with eight graphical electrodes 130 each (labeled electrodes E1-E8 for lead 124 and electrodes E9-E16 for lead 126). Other numbers of leads and electrodes per lead may be displayed as desired. In an implanted system using other numbers of electrodes, that number of electrodes may be shown in lead display panel 104. Up to four groups of leads may be viewed by selecting one of the lead group tabs 132. In addition, an icon 134 representing the case of the IPG 14 is displayed in the lead display panel 104. In addition to allocating current to any of the electrodes of graphical leads 124 and 126, current may be allocated to the case as an electrode.

Each of the electrodes 130 of the leads 124 and 126 may be individually selected, allowing the clinician to set the polarity and the magnitude of the current allocated to that electrode 130. In the illustrated embodiment, electrode E15 is currently selected. Electrical current has been allocated to three groups of electrodes respectively corresponding to three programming areas. Electrode group 130a illustrates a single cathode at electrode E2 to which is allocated 100% of the cathodic current and two anodes at electrodes E1 and E3 to which are allocated 25% and 75% of the anodic current, respectively. Electrode group 130b illustrates a single anode at electrode E7 to which is allocated 100% of the cathodic current and two anodes at electrodes E6 and E8 to which are allocated 50% and 50% of the anodic current, respectively. Electrode group 130c illustrates a single cathode at electrode E10 to which is allocated 100% of the cathodic current and two anodes at electrodes E9 and E11 to which are allocated 60% and 40% of the anodic current, respectively.

The parameter adjustment panel 106 includes a pull-down programming mode field 136 that allows the user to switch between a manual programming mode, an e-troll programming mode, and a Navigation programming mode. As shown in FIG. 4, the manual programming mode has been selected. In the manual programming mode, each of the electrodes 130 of the graphical leads 124 and 126, as well as the graphical case 134, may be individually selected, allowing the clinician to set the polarity (cathode or anode) and the magnitude of the current (percentage) allocated to that electrode 130 using graphical controls located in the amplitude/polarity area 138. In particular, a graphical polarity control 140 located in the area 138 includes a "+" icon, a "−" icon, and an "OFF" icon, which can be respectively actuated to toggle the selected electrode 130 between a positive polarization (anode), a negative polarization (cathode), and an off-state. An amplitude control 142 in the area 138 includes an arrow that can be actuated to decrease the magnitude of the fractionalized current of the selected electrode 130, and an arrow that can be actuated to increase the magnitude of the fractionalized current of the selected electrode 130. The amplitude control 142 also includes a display area that indicates the adjusted magnitude of the fractionalized current for the selected electrode 130. Amplitude control 142 is preferably disabled if no electrode is visible and selected in the lead display panel 104.

The parameter adjustment panel 106, when the manual programming mode is selected, also includes an equalization control 144 that can be actuated to automatically equalize current allocation to all electrodes of a polarity selected by respective "Anode +" and "Cathode −" icons. The parameter adjustment panel 106 also includes a pulse amplitude adjustment control 146 (expressed in milliamperes (mA)), a pulse width adjustment control 148 (expressed in microseconds (μs)), and a pulse rate adjustment control 150 (expressed in Hertz (Hz)), which are displayed in all three of the programming modes. Each of the controls 146, 148, 150 includes a first arrow that can be actuated to decrease the value of the respective stimulation parameter and a second arrow that can be actuated to increase the value of the respective stimulation parameter. Each of the controls 146, 148, 150 also includes a display area for displaying the currently selected parameter. In the illustrated embodiment, a pulse amplitude of 5 mA, a pulse width of 210 μs, a pulse rate of 40 Hz have been selected.

Figure 5:
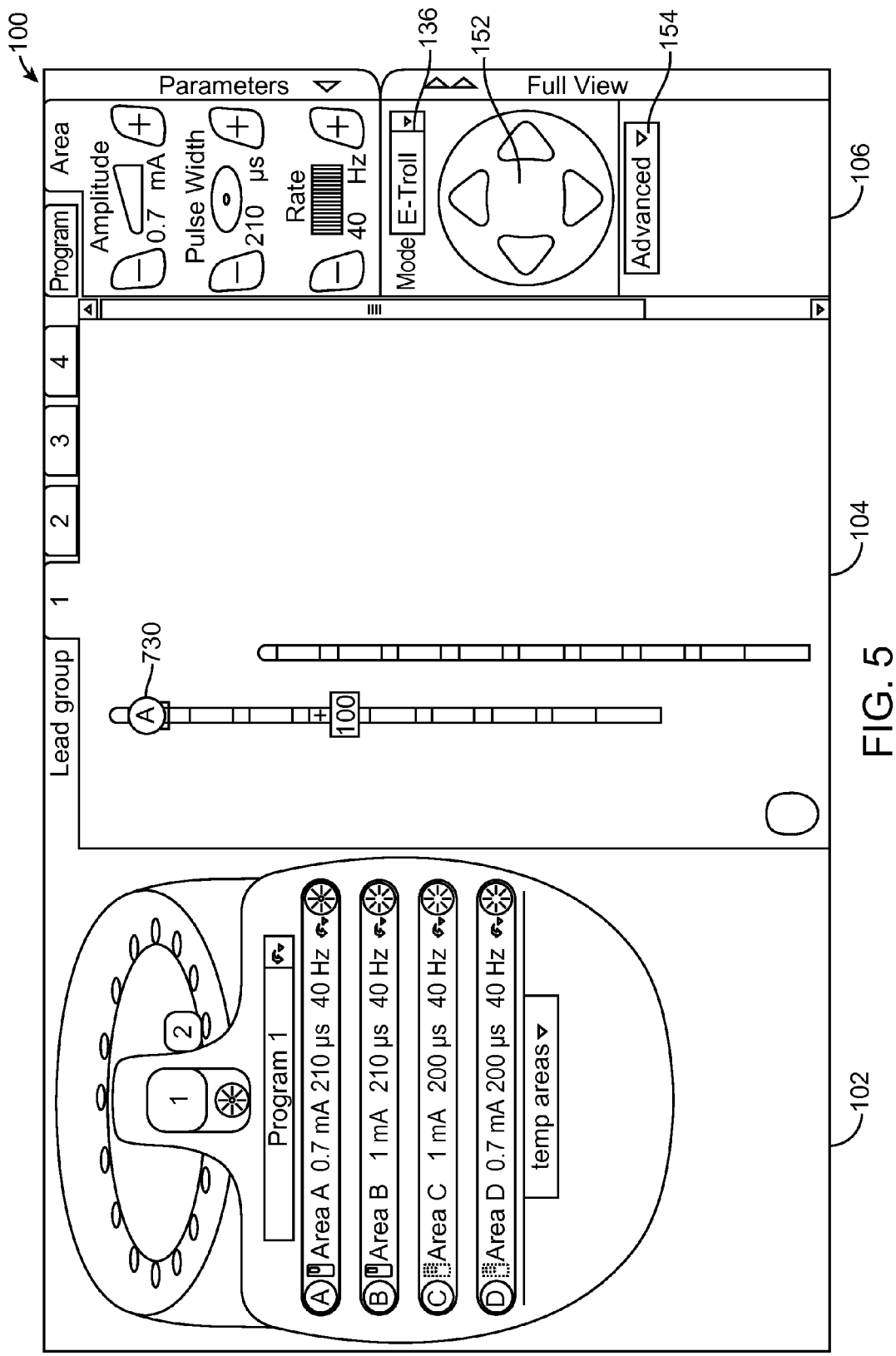
FIG. 5 is a plan view of a user interface of the CP of FIG. 3 for programming the IPG of FIG. 1 in an e-troll mode.

As shown in FIG. 5, the e-troll programming mode has been selected. In this mode, the electrodes 130 illustrated in the lead display panel 104 that were individually selectable and configurable in manual programming mode are used for display only and are not directly selectable or controllable. The parameter selection panel 106 includes a steering array of arrows 152 that allows steering the electrical current up, down, left, or right. In the illustrated embodiment, the electrical current is steered by panning a virtual multipole (i.e., the virtual multipole is moved relative to the actual electrodes 26 without changing the basic configuration (focus (F) and upper anode percentage (UAP)) of the virtual multipole), and computing the electrical amplitude values needed for the actual electrodes 26 to emulate the virtual multipole.

Figure 6:
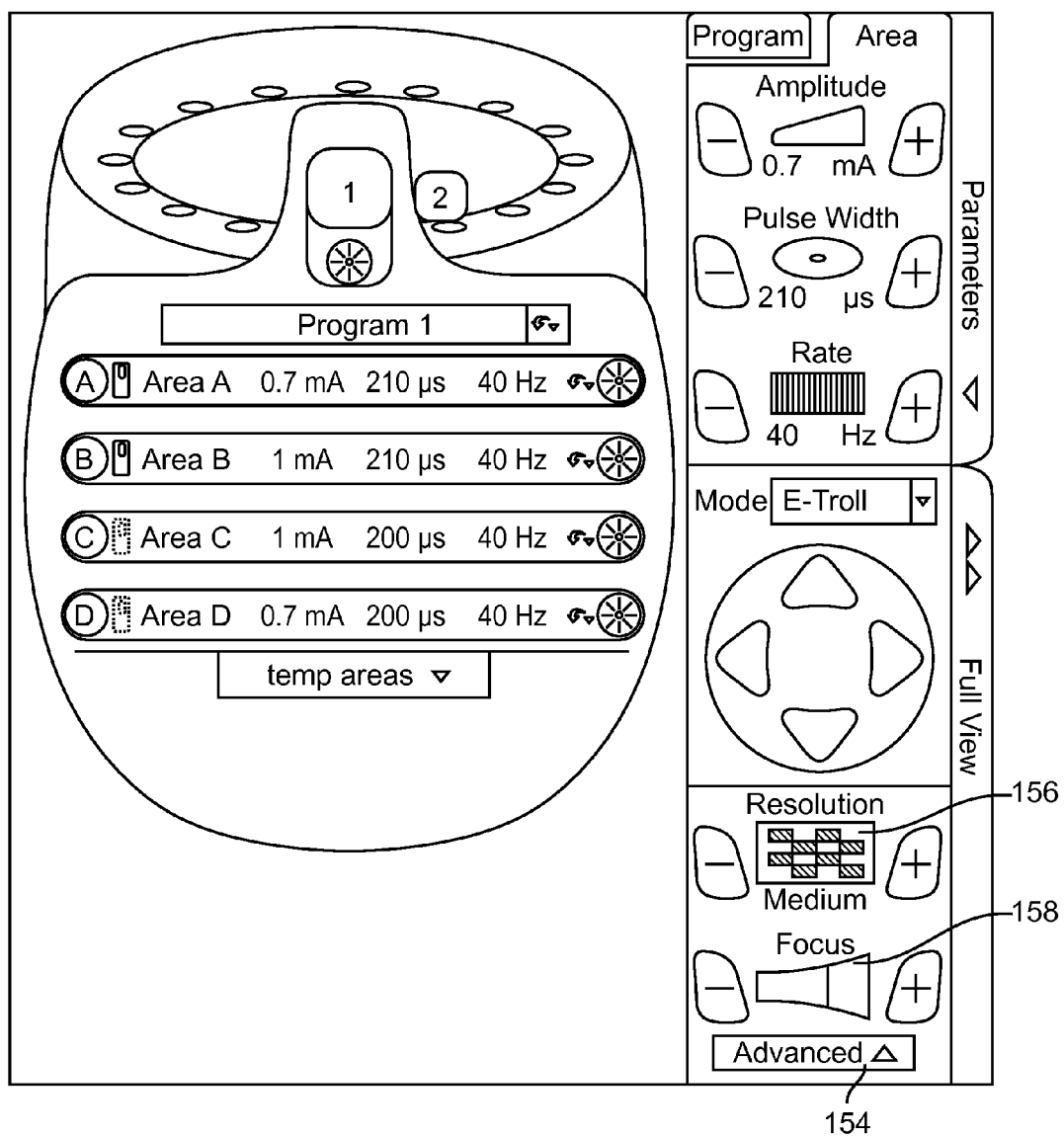
FIG. 6 is a plan view of the user interface of FIG. 5, particularly showing the expansion of the Advanced Tab into resolution and focus controls.

In the e-troll programming mode, the parameter adjustment panel 106 also includes an advanced tab 154, which when actuated, hides the lead display panel 104 and provides access to a resolution control 156 and a focus control 158, as shown in FIG. 6. The resolution control 156 allows changing the stimulation adjustment resolution. In one embodiment, three possible settings of Fine, Medium, and Coarse may be chosen. The resolution control 156 has a "+" icon and a "−" icon that can be used to adjust the resolution. The resolution control 156 also includes a display element that graphically displays the current resolution level. When the resolution is set to Fine, each change caused by use of the steering array 152 makes less of a change to the electrode configuration than when the resolution is set to Medium or Coarse. For example, panning of the virtual multipole with a Coarse resolution may displace the virtual multipole relative to the electrode array 26 in steps equivalent to 10% of the electrode spacing, whereas panning of the virtual multipole with a Fine resolution may move the virtual multipole relative to the electrode array 26 in steps equivalent to 1% of the electrode spacing.

The focus control 158 allows changing the stimulation focus by displacing the anode(s) and cathode of the virtual multipole toward each other to increase the focus, or displacing the anode(s) and cathode of the virtual multipole away from each other to decrease the focus. The focus control 158 has a "+" icon and a "−" icon that can be used to adjust the focus. The resolution control 158 also includes a display element that graphically displays the current focus level.

Figure 7:
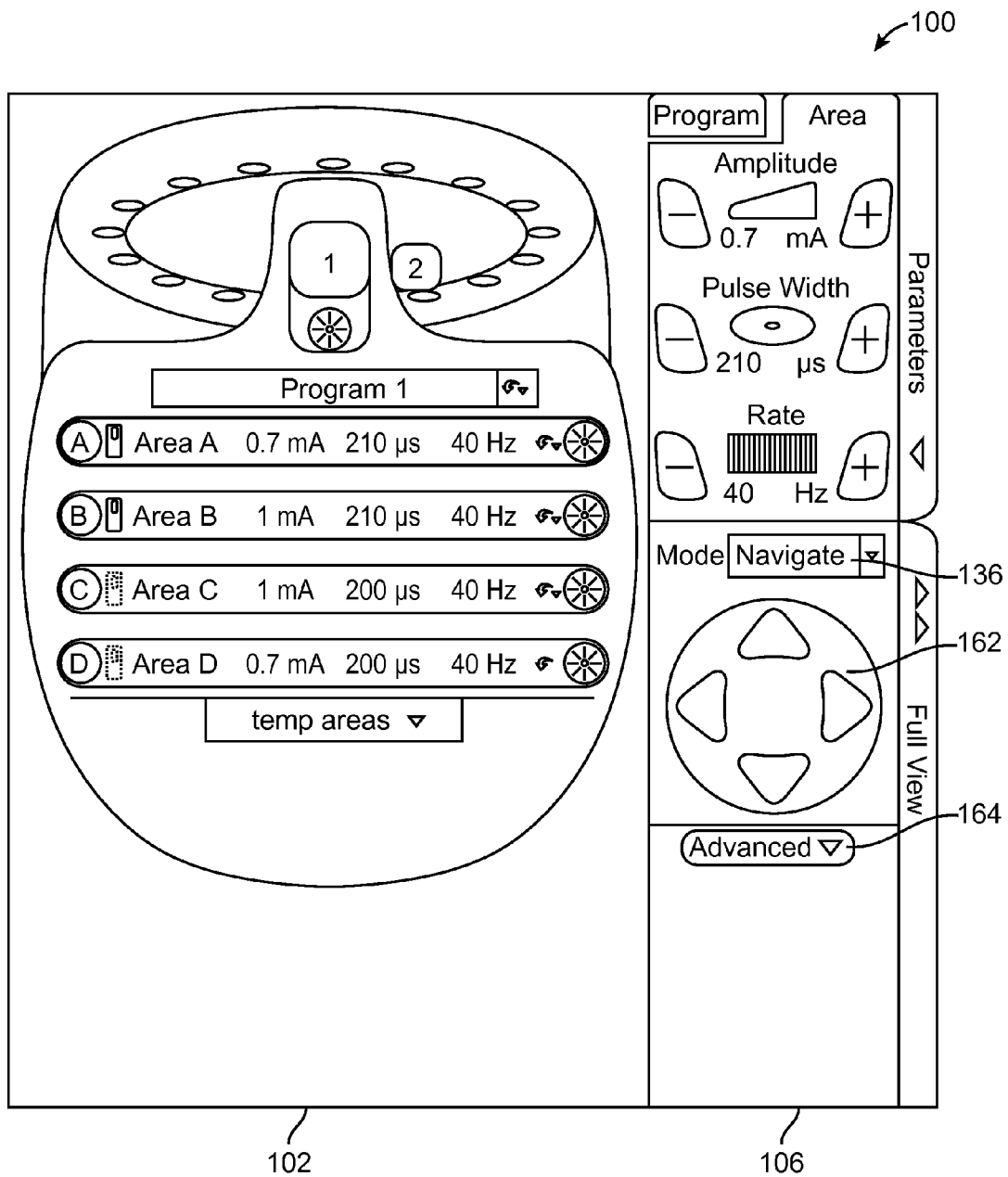
FIG. 7 is a plan view of a user interface of the CP of FIG. 3 for programming the IPG of FIG. 1 in a Navigation mode.

As shown in FIG. 7, the Navigation programming mode has been selected. As in the e-troll programming mode, in the Navigation programming mode, the electrodes illustrated in the lead display panel 104 that were individually selectable and configurable in manual programming mode are used for display only and are not directly selectable or controllable. The parameter selection panel 106 includes a steering array of arrows 162 that allows steering the electrical current up, down, left, or right. In the illustrated embodiment, the electrical current is steered by weaving one or more anodes around the cathode of the virtual multipole as the cathode is displaced relative to the electrode array 26, and computing the electrical amplitude values needed for the electrodes 26 to emulate the virtual multipole.

Programming sessions for tissue stimulators may involve a series of pre-programming steps followed by a series of programming steps. During the pre-programming steps, stimulation is typically turned off. While information may be retrieved from the neurostimulator, or IPG 14, during the pre-programming steps, no programming information is transmitted to the IPG 14. Pre-programming steps may include connecting to the tissue stimulator, downloading data from the tissue stimulator, performing tissue stimulator checks, entering initial programming parameters, entering initial electrode configurations, and the like.

After the pre-programming steps, the programming steps are performed. During programming, stimulation is typically turned on, and applied in accordance with a variety of different stimulation parameter sets. That is, during the programming steps, information, such as stimulation parameter changes, is transmitted from the CP 18 to the IPG 14. At the conclusion of the programming steps, the stimulation parameter sets that are determined to be the most efficacious are uploaded to the IPG 14 and/or to the RC 16.

Most pertinent to the present inventions, steps that are commonly performed during a programming session may be pre-programmed into the programming package 84 as a series of steps that are automatically performed without requiring user input. The control circuitry 80 is configured for performing the series of steps without requiring user input while the steps are being performed. Such an automated series of steps may be particularly advantageous during the pre-programming phase of a programming session. Automating the series of pre-programming steps eliminates the time spent by a clinician to manually execute steps that perform data download, stimulator checks, and/or other initial setup steps. This allows the clinician to perform other tasks during programming session setup steps, and to optimize use of patient interface time. Automating a series of pre-programming steps also simplifies the setup of a neurostimulator programming session by automating access to a particular screen with pre-determined initial parameter settings. It should be well understood that the CP 18 may additionally or alternatively be configured to automatically perform a series of programming steps.

A software interface in accordance with the present invention allows clinicians to use a pre-defined or custom-designed series of pre-programming steps that are automatically performed in order to reach a pre-defined parameter set or step through a series of configurations during a preprogramming session. The series of steps can be used to automatically complete a part of a pre-programming session, or the entire pre-programming session, depending on the complexity of the steps, the requirements of the clinician, or the therapy. The pre-programming sequence is automated so that commonly-used steps can be performed quickly and easily. The software may be configured to perform button clicks, screen transitions, or retries as necessary to automatically complete the series of steps. Wait times may be incorporated between steps.

Figure 8:
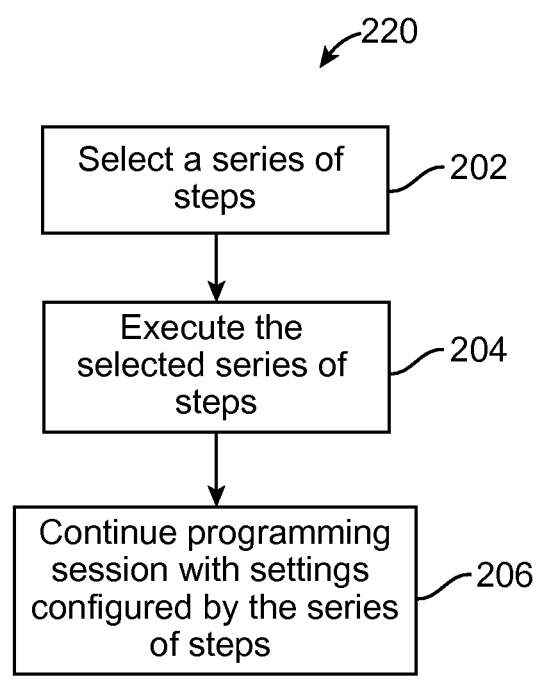
FIG. 8 is a flow chart of a method for programming a neurostimulator.

A method 200 for selecting a series of pre-programming steps will be described with reference to FIG. 8. First, in step 202, a series of pre-programming steps is selected from among a plurality of series available in the memory 82 of the CP 18. The selection is made in response to input from the user. For example, the user may select the desired series from a menu of available series by actuating a button, or other such control element, on the user interface of the CP 18. In alternative embodiments, each series available on the CP 18 may also include programming steps in addition to the different series of pre-programming steps.

The plurality of series available in the memory 82 of the CP 18 may include a series of automated steps for SCS, a series of automated steps for DBS, a series of automated steps for FES, a series of automated steps for ONS, series of automated steps for PNS, a series of automated steps for PNFS, a series of automated steps for VNS, a series of automated steps for ONS (e.g., for the treatment of headaches), and the like. The plurality of series available in the memory 82 may alternatively or additionally include a series of automated steps for treating chronic pain, a series of automated steps for treating Parkinson's disease, a series of automated steps for treating headaches, a series of automated steps for treating paralysis, and the like. Thus, the selection of the desired series of steps may be based upon target tissue and/or a condition being treated.

In one embodiment, the CP 18 is configured for determining the location of the neurostimulation leads 12, and thus the tissue to be treated. The selection of the desired series of steps may be based on this determination. Further details regarding a system and method for determining the location of an implanted lead can be found in U.S. Application Ser. No. 61/611,840, entitled "System And Method For Estimating Location And Depth Of Stimulation Leads," which is expressly incorporated herein by reference.

Next, in step 204, the control circuitry 80 automatically performs the selected series of pre-programming steps; that is, the control circuitry 80 is configured for performing the selected series of steps without requiring input from the user while the series of steps is being performed.

Figure 9:
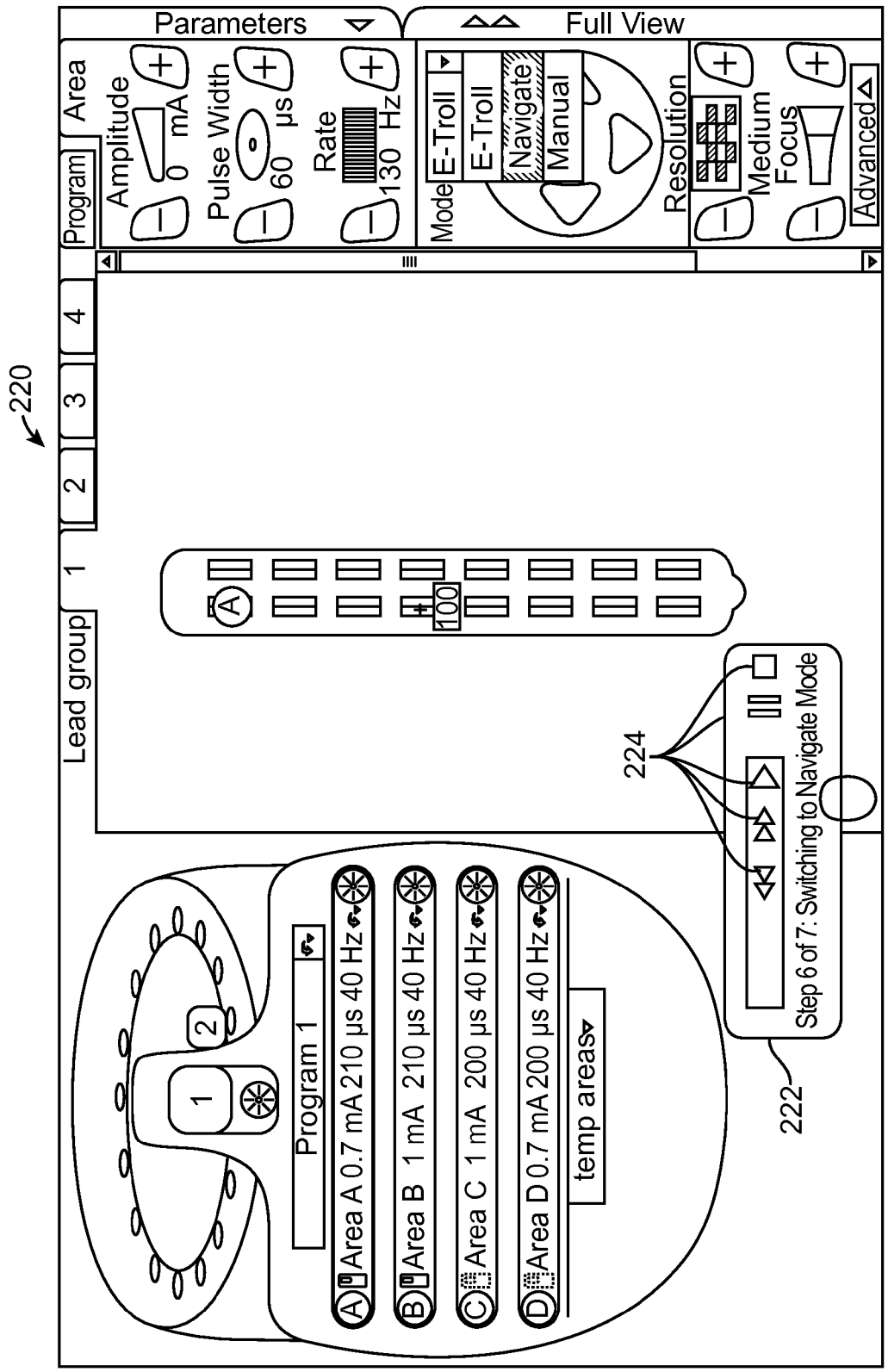
FIG. 9 is a programming screen displayed by the clinician programmer of FIG. 3 showing the status of the series of steps being automatically performed.

The user interface of the CP 18 may be configured for displaying an indication of which step in the series is currently being performed. FIG. 9 depicts a graphical user interface (GUI) 220 that can be generated by the CP 18 while the series of steps is automatically being performed. In the illustrated embodiment, the GUI 220 displays the step 222 in the selected series that is currently being performed. In the example shown in FIG. 9, the current step 222 is "switching to navigation mode." The current step 222 is depicted in phantom over the programming screen. Alternatively, the GUI 220 may display which step is currently being performed by showing a status bar, or the like.

The GUI 220 also includes control buttons 224 configured for being actuated, so that the user may intervene, if desired or necessary, while the series of steps is being automatically performed. For example, the user may stop, pause, restart, repeat, or skip one or more of the steps in the series by actuating one or more of the control buttons 224. In an optional embodiment, any time during the current pre-programming process, a control button can be configured for being actuated to call up another series of steps that can be automatically performed. In another optional embodiment, when the series of steps are paused, the user can select a breakpoint at the paused step, perform other actions in the GUI 220 outside of the pre-programming series of steps, and then return to the paused step.

Figure 10:
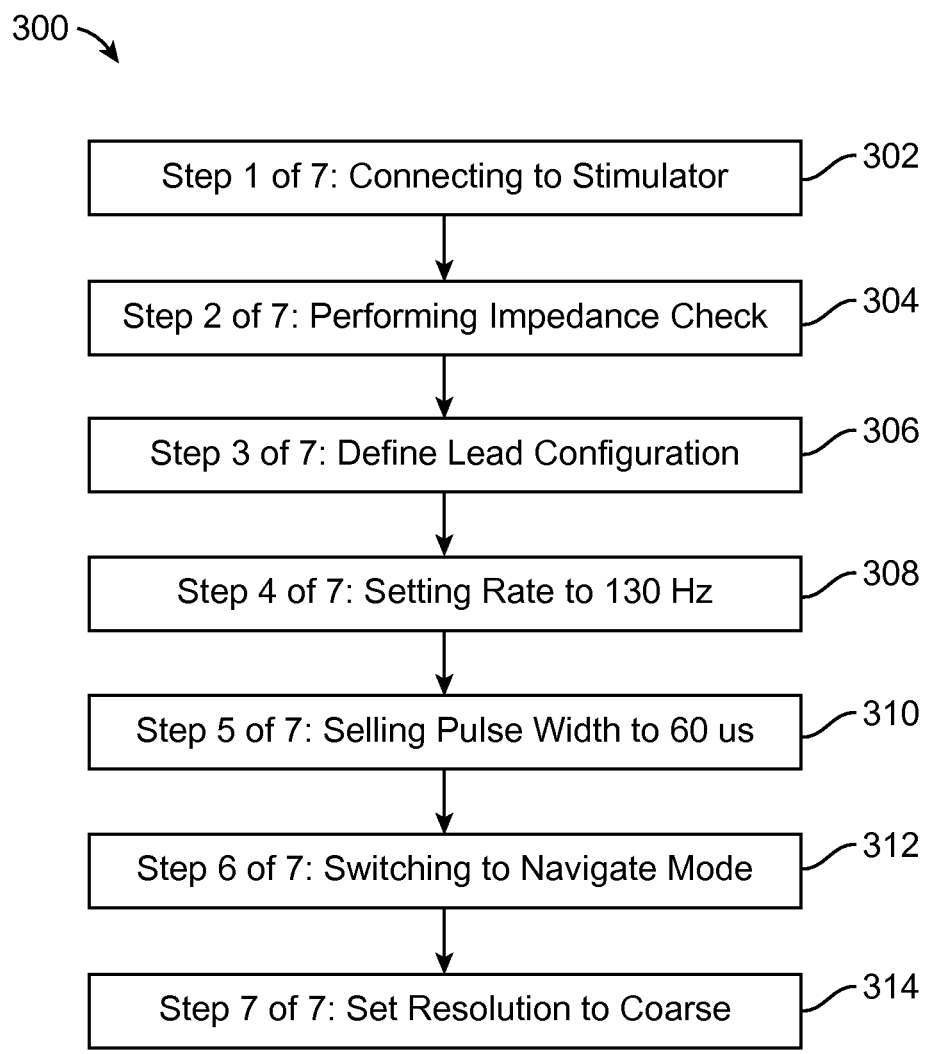
FIG. 10 is a flowchart depicting a series of automated steps to be performed by the clinician programmer of FIG. 3.

An exemplary series 300 of pre-programming steps is illustrated in FIG. 10. The series 300 of pre-programming steps includes connecting the CP 18 to the IPG 14 (step 302), performing an impedance check of the electrodes 26 (step 304), defining a lead configuration (step 306), setting an initial pulse rate (step 308) for the subsequent programming session, setting an initial pulse width (step 310) for the subsequent programming session, setting the subsequent programming session to "navigation mode" (step 312), and setting the current steering resolution for the navigation mode to coarse (step 314).

The steps included in the automated series of pre-programming steps are not limited to those shown in FIG. 10. It should be well understood that the automated series of steps may include other pre-programming steps in addition to, or instead of, the pre-programming steps depicted in FIG. 10. For example, besides pulse rate and pulse width, the series may alternatively or additionally include a step of defining one or more other initial programming parameters, such as pulse amplitude, pulse shape, pulse waveform, and/or pre-pulsing. As another example, instead of setting the subsequent programming session to "navigation mode," the series may alternatively include a step of setting the subsequent programming session to "E-Troll" mode or "manual" mode. As still another example, instead of setting the current steering resolution for the navigation mode or E-Troll mode to coarse, the series may alternatively include a step of setting the current steering resolution to medium or fine. The series may additionally set other current steering parameters, such as focus, start point, end point, directionality, path (for example, the user may trace a desired current steering path), or the like. In still another example, in the case where the subsequent programming session is set to "manual mode," the series may include a step of defining an electrode configuration, which may include anode and cathode placement, and/or current fractionalization. In yet another example, the series may include a step of defining at least one stimulation limitation, such as maximum pulse amplitude, minimum pulse amplitude, maximum pulse width, minimum pulse width, maximum pulse rate, minimum pulse rate, or the like.

In one embodiment, one of the steps in the automated series of steps includes obtaining a physiological measurement of, for example, monopolar impedance, blood flow, imaging, chemical sensors, or the like. Based on the measurement, the CP 18 may be configured to change other steps in the series, change the order of other steps in the series, add a step to the series, and/or remove a step from the series. For example, based on an impedance measurement, the CP 18 may be configured to adjust an amplitude parameter in one of the other steps in the series.

In addition to, or alternative to, the exemplary pre-programming steps described above, the automated series of steps may include programming steps. For example, the automated series of steps may include a programming sequence, a series of parameters, and/or a series of electrode configurations.

The series of steps to be automatically performed may be pre-defined within the software. That is, the series may be pre-programmed and included when the software is installed. Alternatively, the series of steps may be custom-designed. For example, a series of steps may be custom-designed by making a copy of a pre-defined series of steps and adding or removing steps. In another example, a series of steps may be custom-designed by combining functions available in the software to form a sequence of steps to execute through the software interface. A custom-designed series of steps may incorporate a pre-defined series of steps. Steps may be created by selecting from a list of software functions, copying a step or series of steps from an existing series of steps, or the like. As such, the programming package 84 may include a tool for allowing a clinician to create a custom-designed series of automated steps, based on preferences unique to that clinician.

A series of steps may be customized by using a record and play back tool. In this embodiment, a user performs a plurality of steps during a programming procedure for a patient. The CP 18 records the plurality of steps performed by the user. That is, the CP 18 may record each button click, screen transition, data input, etc. needed to complete the plurality of steps. The plurality of recorded steps is stored in the CP 18. During a programming procedure for a subsequent patient, the user may want the plurality of recorded steps to be performed. Thus, the user may choose the plurality of recorded steps from among the series of steps available on the CP 18, which causes the CP 18 to automatically perform the plurality of recorded steps. That is, the plurality of recorded steps may automatically be initiated in response to actuation of one or more control buttons, and once initiated, requires no further input from the user to perform the steps.

Finally, referring back to FIG. 8, the programming session is continued in step 206. The settings configured by performing the selected series of steps serve as a starting point for the clinician to perform additional programming steps during the programming session. After the programming session is completed, the desired stimulation parameter sets are uploaded to the neurostimulator and/or to the RC 16.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for programming a neurostimulator in communication with the external control device, comprising:
output circuitry;
control circuitry configured for cooperating with the output circuitry to program the neurostimulator and for automatically performing a series of steps used to program the neurostimulator to deliver a therapy; and
a user interface including one or more control elements configured for being actuated during the automatic performance of the series of steps to prompt the control circuitry to pause, stop, restart, skip, or repeat one of the steps in the series of steps used to program the neurostimulator to deliver the therapy.

2. The external control device of claim 1, wherein the user interface includes a monitor configured for displaying which step in the series is currently being performed.

3. The external control device of claim 1, further comprising memory configured for storing a plurality of different series of steps, wherein the user interface includes another one or more control elements configured for being actuated to prompt the control circuitry to select the series of steps from the stored plurality of series of steps.

4. The external control device of claim 1, wherein the user interface comprises one or more of a mouse, a trackball, a touchpad, and a joystick configured for allowing the user to actuate the one or more control elements.

5. The external control device of claim 1, wherein the user interface comprises a digitizer screen configured for allowing the user to actuate the one or more control elements.

6. The external control device of claim 1, wherein the series of steps is a series of pre-programming steps, and the user interface includes another one or more control elements configured for being actuated to prompt the control circuitry to program the neurostimulator after the series of pre-programming steps is performed.

7. The external control device of claim 6, wherein one of the preprogramming steps comprises defining one or more initial programming parameters selected from the group consisting of:
pulse amplitude, pulse width, pulse frequency, pulse shape, pulse waveform, and pre-pulsing.

8. The external control device of claim 6, wherein one of the preprogramming steps comprises defining a configuration of a lead coupled to the neurostimulator.

9. The external control device of claim 6, wherein one of the preprogramming steps comprises defining at least one current steering parameter selected from the group consisting of:
resolution, focus, start point, end point, directionality, and path.

10. The external control device of claim 6, wherein one of the preprogramming steps comprises defining an electrode configuration.

11. The external control device of claim 6, wherein one of the preprogramming steps comprises defining at least one stimulation limitation selected from the group consisting of:
maximum pulse amplitude, minimum pulse amplitude, maximum pulse width, minimum pulse width, maximum pulse rate, and minimum pulse rate.

12. An external control device for programming a neurostimulator in a programming session that includes pre-programming steps followed by programming steps, the external control device including:
output circuitry;
control circuitry configured for cooperating with the output circuitry to program the neurostimulator and for automatically performing a series of steps used to program the neurostimulator to deliver a therapy, wherein the automatically-performed series of steps includes at least sonic of the pre-programming steps or at least some of the programming steps; and
a user interface including one or more control elements configured for being actuated during the automatic performance of the series of steps to prompt the control circuitry to pause, stop restart, skip, or repeat one of the steps in the series of steps used to program the neurostimulator to deliver the therapy.

13. The external control device of claim 12, wherein the user interface is configured display buttons configured for actuation by a user to prompt the control circuitry to pause, stop, restart, skip, or repeat one of the steps in the series of steps.

14. The external control device of claim 12, wherein the user interface is configured to simultaneously display pause, stop, restart, skip and repeat buttons.

15. The external control device of claim 12, wherein the user interface includes a monitor configured for displaying which step in the series is currently being performed.

16. The external control device of claim 12, wherein the wherein the automatically-performed series of steps includes at least some of the pre-programming steps.

17. The external control device of claim 12, wherein the external control device is configured to present a plurality of series of steps to a user, and receive a user selection of a selected one of the plurality of series.

18. The external control device of claim 17, wherein the plurality of series include a series of steps for spinal cord stimulation (SCS) or a series of steps for deep brain stimulation (DBS).

19. The external control device of claim 17, wherein the plurality of series include series of steps based on tissue to be targeted.

20. The external control device of claim 17, wherein the plurality of series include series of steps based on condition to be treated.

* * * * *